United States Patent [19]
Linn et al.

[11] Patent Number: 5,597,696
[45] Date of Patent: Jan. 28, 1997

[54] COVALENT CYANINE DYE OLIGONUCLEOTIDE CONJUGATES

[75] Inventors: C. Preston Linn; J. Bruce Pitner; Pat D. Mize, all of Durham, N.C.

[73] Assignee: Becton Dickinson and Company, Franklin Lakes, N.J.

[21] Appl. No.: 276,238

[22] Filed: Jul. 18, 1994

[51] Int. Cl.$^6$ ............................. C12Q 1/68; C07H 21/04
[52] U.S. Cl. ........................... 435/6; 536/26.6; 250/458.1
[58] Field of Search .............................. 536/26.6; 435/6; 250/458.1, 461.1, 461.2

[56] References Cited

U.S. PATENT DOCUMENTS 4,883,867  11/1989  Lee et al. .................................. 536/28

OTHER PUBLICATIONS

Haralambidis et al. (1987) Nucleic Acids Res. 15(12):4857–4876.

Primary Examiner—Scott W. Houtteman
Attorney, Agent, or Firm—David W. Highet, Esq.

[57] ABSTRACT

The present invention relates to conjugates of a cyanine dye and an oligonucleotide. When these conjugates hybridize or bind to a target, a detectable increase in fluorescence intensity or change in fluorescence polarization is observed.

10 Claims, 1 Drawing Sheet

COVALENT CYANINE DYE OLIGONUCLEOTIDE CONJUGATES

FIELD OF THE INVENTION

The present invention relates to the covalent attachment of thiazole orange and other related labels to oligonucleotides which are utilized in the detection of nucleic acid targets.

BACKGROUND OF THE INVENTION

The detection of single-stranded nucleic acid targets by hybridization to fluorescently labeled probes is of significant interest for the development of improved reagents for molecular diagnostics. Fluorescently labeled oligonucleotides also are useful probes of nucleic acid structure and hybridization at concentrations below those detectable by other non-isotopic analytical solution-phase methods. Morrison, L. E, and Stols, L. M., *Biochemistry* 32, 3095 (1993).

Cyanine dyes such as thiazole orange have demonstrated large fluorescence intensity increases upon binding to double stranded DNA. Makler, M. T., Lee, L. G., and Rectenwald, D. (1987) *Cytometry* 8, 568–570; Lee, L. G., Chen, C-H., and Chiu, L. A. (1986) *Cytometry* 7, 508–517; Lee, L. G. and Chen, C-H., U.S. Pat. No. 4,957,870 (Sep. 18, 1990) "Detection of Reticulocytes, RNA, and DNA"; Lee, L. G. and Chen, C-H., U.S. Pat. No. 4,883,867 (Nov. 28, 1989) "Detection of Reticulocytes, RNA, and DNA". This fluorescence intensity enhancement for thiazole orange has been estimated to be as high as 18,000. Glazer, A. N. and Rye, H. S., *Nature* 359, 859 (1992). Although covalently linked dye-oligonucleotide complexes have been used to configure assays based on fluorescence energy transfer and quenching, direct tethering of a cyanine dye to an oligonucleotide has not been accomplished to date.

SUMMARY OF THE INVENTION

The present inventors have addressed this discrepancy in the art by directly tethering cyanine dyes to oligonucleotides to produce covalent cyanine dye-oligonucleotide conjugates. When these conjugates hybridize or bind to a target, a fluorescence intensity increase and/or polarization is observed.

BRIEF DESCRIPTION OF THE DRAWINGS

The various objects, advantages and novel features of the invention will be more readily appreciated from the following detailed description when read in conjunction with the appended drawing figure in which.

DETAILED DESCRIPTION OF THE INVENTION

Figure 1:
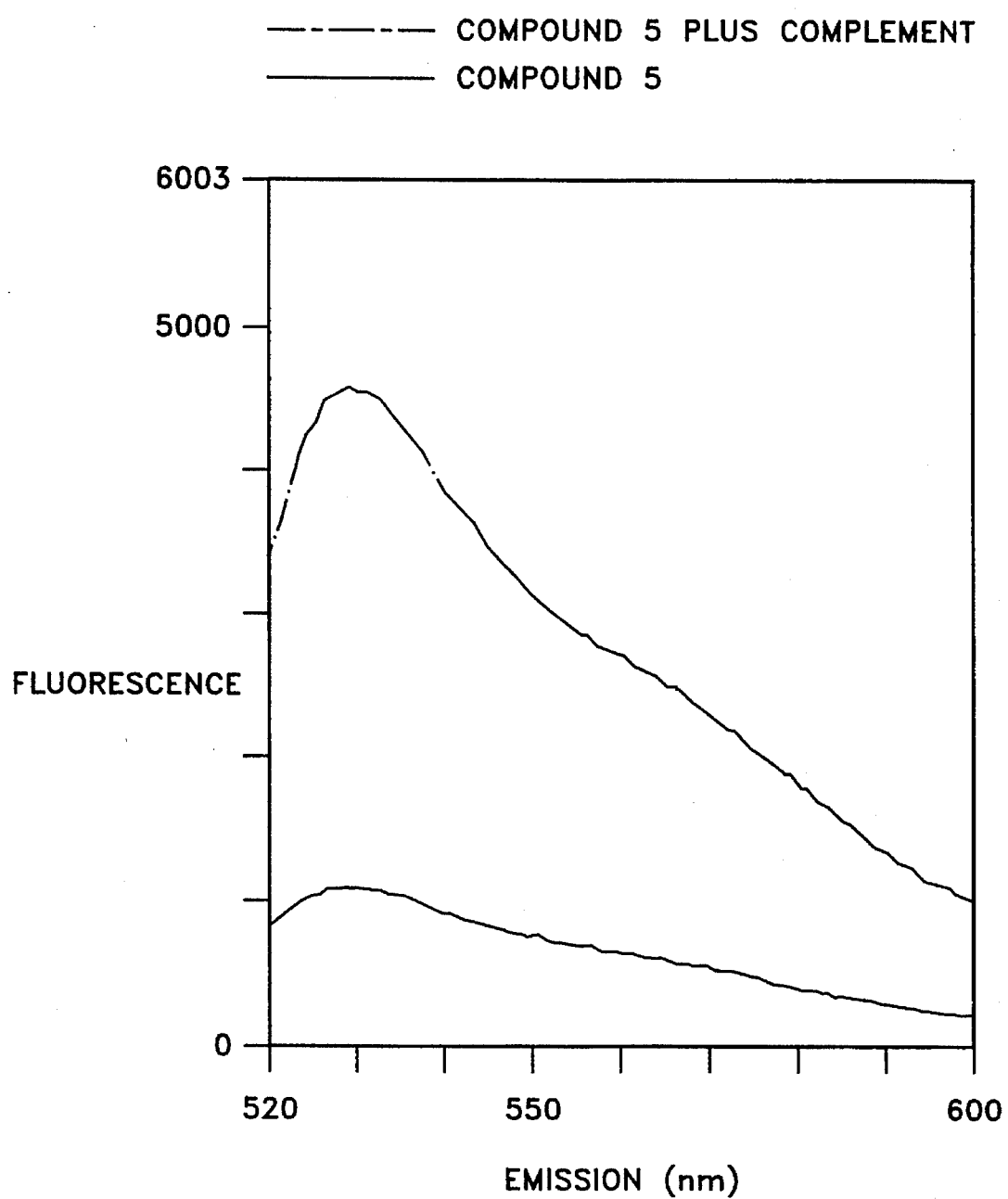
FIG. 1 is a graphic depiction of the results of a fluorescence polarization assay with a thiazole-orange labeled oligonucleotide and its complement.

Oligonucleotides are utilized in a variety of formats to determine the presence or absence of a particular target of interest. In one format, an oligonucleotide is utilized as a probe to detect a target nucleic acid sequence by hybridizing thereto and thus forming a double stranded or partially double stranded product. In another format, an oligonucleotide known as a nucleic acid ligand or aptamer binds a protein or small molecular target by means other than Watson-Crick type nucleotide hybridization, as taught in U.S. Pat. No. 5,270,163. Similarly, compounds which bind to protein or small molecular targets have been produced by linking two or more oligonucleotides of reverse sequence polarity to a connecting compound. These oligonucleotide compounds are referred to as bi-directional nucleic acid ligand compounds and are more completely described in co-pending U.S. patent application Ser. No. 08/252,071, filed May 31, 1994.

The present invention relates to the covalent linking of a cyanine dye to an oligonucleotide (oligonucleotide when used herein is intended to include all oligonucleotide containing compounds including those described above). Upon hybridization or binding of this dye-oligonucleotide conjugate to a target, whether nuclei(acid sequence, protein or small molecule, changes in fluorescence may be detected by either steady state intensity or life time measurements. Hybridization or binding of conjugate to target may also be detected by other fluorescence techniques such as anisotropy or energy transfer techniques.

Suitable cyanine dyes for use in the present invention include those described in U.S. Pat. No. 4,883,867 and having the following structure:

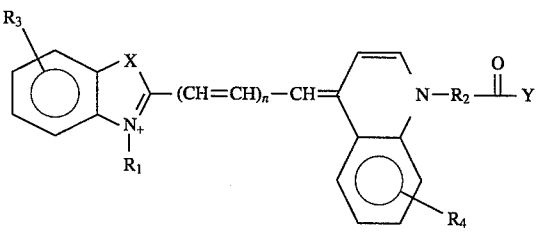

where X is O, S, Se, N-alkyl (having 1–6 carbons) or $C(CH_3)_n$; $R_1$ is alkyl having from 1–6 carbons; $R_2$ is alkyl having from 1–6 carbons; $R_3$ is fused benzene, alkyl (having 1–6 carbons), methoxy or is absent; $R_4$ is alkyl having 1–6 carbons, methoxy or is absent; and Y is a reactive ester such as N-hydroxysuccinimide or pentafluorophenyloxy acid chlorides; and n is zero or an integer from 1–6. Some of the dyes represented by this structure are thiazole orange and thiazole yellow.

Suitable linkers or tethers for combining the dye and oligonucleotide include any linking compound which will bind to the dye through an amide bond. Generally, the tethers are hydrocarbon chains of from 2 to 10 carbons in length which are commercially available from companies such as Glen Research, and are referred to as linker arms.

The oligonucleotides to which the cyanine dyes are linked are single stranded and generally contain between 8 and 50 bases. The oligonucleotides may be composed of ribonucleotides, deoxyribonucleotides, ribonucleotide derivatives, deoxyribonucleotide derivatives, or combinations thereof. Such oligonucleotides are well known in the art and can be prepared with commercially available nucleic acid synthesizers such as the 380B DNA synthesizer which is commercially available from Applied Biosystems of Foster City, Calif.

In order to prepare cyanine dye-oligonucleotide conjugates of the present invention, the oligonucleotide is reacted with an appropriate linker or tether as a phosphoramidite reagent such that the linker covalently attaches to the oligonucleotide at its 5' end. Similarly, the linker can be covalently attached to an oligonucleotide at its 3' end or internally by tethering directly to a pyrimidine or purine ring using methods known by those in the art. A related method for internal labeling using isothiocyanate derivatives is described in a co-pending United States Patent Application filed on the same date herewith and assigned Ser. No.

08/276,271 and as described by Goodchild, J. (1990) *Bioconjugate Chem.* 1, 165–187. When a protected amine linker arm is used (attached at the 5' or 3' end, or through a purine or pyrimidine), the resultant product is then deprotected with an appropriate base such as ammonium hydroxide to leave a primary amine at the end of the linker. This resultant molecule is reacted with the cyanine dye under basic conditions and then purified by being passed through an appropriate column for example to remove unreactive dye and unlabeled oligonucleotide.

Using fluorescence intensity measurements, life time fluorescence changes, or anisotropy, measurable differences can be detected between the single stranded cyanine dye-oligonucleotide conjugate and the product when this conjugate hybridizes to a nucleic acid target or binds to a protein or small molecular target. Generally a two-fold or greater fluorescence intensity increase is observed after hybridization of a single stranded oligonucleotide-cyanine dye conjugate to a complimentary unlabeled oligonucleotide. Fluorescence lifetime changes may also be observed and can be determined using dynamic fluorescence techniques. Significant changes in fluorescence polarization and anisotropy upon binding of the single stranded oligonucleotide-cyanine dye conjugates to oligonucleotides and other target molecules may also be used as means to detect the presence of these analytes. In addition to these qualitative differences between single stranded conjugate and double stranded product or bound target, quantitative values may also be obtained.

One particularly useful form of fluorescence assay is the utilization of fluorescence polarization. Fluorescence polarization occurs when a fluorescent molecule is excited with polarized light which causes the emitted light from the fluorescent molecule to also be polarized. A quantitative determination of the polarization of the excited molecule can be determined by measuring the relative intensity of the emitted light parallel to and perpendicular to the plane of polarized light. An advantage of this type of assay is that it is homogeneous, that it does not require any separation steps.

In such a polarization assay, polarizers are placed in the excitation beam and the emitted beam is measured through two polarizers; one parallel to the excitation polarizer and one perpendicular to the excitation polarizer. Polarization will be maximized if no molecular motion occurs and will be minimized if complete randomization occurs. These polarization assays measure rotational diffusion rates. Rotational diffusion rates relate to the size of the molecular species, that is smaller species rotate more rapidly than do larger species. Dynamic anisotropy and lifetime measurements are made by analyzing the decay of fluorescence intensity. These may be made either in the time domain (pulse method) or in the frequency domain (phase modulation method). Dynamic anisotropy measurements can be used to determine rotational correlation times. In general this value becomes larger as the rotational diffusion rate becomes slower. This increase can be correlated to binding of single stranded oligonucleotide-cyanine conjugates to target molecules.

Polarization and anisotropy are also defined mathematically by the following equations:

$$P(\text{polarization}) = \frac{Ipa - Ipe}{Ipa + Ipe}$$

$$r(\text{anisotropy}) = \frac{Ipa - Ipe}{Ipa + 2Ipe}$$

where Ipa is parallel intensity and Ipe is perpendicular integrity. The relationship between anisotropy (r) and polarization (P) is also described by the equation:

$$r = \frac{2P}{3 - P}$$

The invention is further described by the following examples which are offered by way of illustration and are not intended to limit the invention in any manner. In these examples all percentages are by weight if for solids and by volume if for liquids or are used to refer to reaction yields, and all temperatures are in degrees Celsius unless otherwise noted.

EXAMPLE 1

Preparation of Thiazole Orange-Oligonucleotide Conjugates

In this example oligodeoxynucleotides were prepared using an ABI380 B automated synthesizer (Applied Biosystems, Inc., Foster City, Calif.) using standard reagents supplied by the manufacturer, and purified by standard denaturing polyacrylamide gel electrophoresis techniques unless otherwise noted. The 5'-aminohexyl (C6) phosphoramidite reagent (ABI Aminolink 2™) was obtained from ABI. The 5'-aminopropyl (C3) linker phosphoramidite reagent was obtained from Glen Research (Sterling, Va.; product number 10-1903-90).

NMR spectra for the compounds synthesized in the example were recorded on an IBM/Brucker WP-200SY (200 mHz) (Billerica, Mass.). High resolution fast atom bombardment (FAB) mass spectra (AIG, Inc., Raleigh, N.C.) were obtained with a high performance double focusing AMD 604 instrument with a resolution of 8000 amu. Low-resolution positive ion FAB mass spectra (FAB+) were obtained with a VG Trio-2 quadrupole instrument using either a glycerol or m-nitrobenzyl alcohol sample matrix. Preparative TLC was performed on glass-backed reverse phase PLKC18F silica gel plates (Whatman). UV/Vis spectra were obtained with a Hewlett Packard HP 8452A Spectrophotometer equipped with an HP 89090A cell controller for variable temperature experiments.

Preparation of Thiazole Orange ("TO") N-hydroxysuccinimide ester 3-(1-(4-methyl-quinolinium))-propionic acid (1). Lepidine (2.95 gm, Aldrich) was mixed with 4.13 gm iodopropionic acid (Aldrich) neat. This mixture was heated at 80° C. for three hours under argon in an oil bath. The solid that formed was triturated with dicholoromethane and collected by filtration to give compound 1 as 5.2 gm of yellow solid (73%): $^1$H NMR (DMSO-$d_6$): ppm 3.01 (s,3H), 3.08 (t, 2H), 5.21 (t, 2H), 8.07 (m, 2H), 8.28 (t, 1H), 8.57 (dd, 2H), 9.43 (d, 1H), 12.5 (br s, 1H); $^{13}$C NMR (DMSO-d6) ppm 19.8, 33.3, 52.8, 119.2, 122.4, 127.2, 128.9, 129.5, 135.2, 136.7, 149.3, 159.0, 171.4; LRMS (FAB$^+$, glycerol)M+=216 m/z.

(4-[3-methyl-2,3-dihydro-(benzo-1,3-thiazole)-2-methylidene]-1-quinolinium)-3-propionic acid (2). 1-(4-Methylquinoline)-propionic acid (1.0 g) and 1.0 g N-methyl-benzothiazolethiomethyl tosylate (Bader) were mixed together in 15 ml ethanol in a 50 mL round bottom flask. Triethylamine (0.1 mL) was added. Almost immediately the reaction mixture turned bright red. The reaction mixture was heated at reflux for two hours and cooled to room temperature. A red solid was isolated from the resulting (and foul smelling) solution. The yield of this material was 900 mg (47%) and only showed one spot near the origin on thin layer chromatography (silica gel, 9:1 dichloromethane/methanol).

NMR (CD$_3$OD) $^1$H ppm: 1.31 (t, 2H), 2.86 (t, 2H), 3.20 (t, 2H), 3.31 (s, 2H), 3.90 (s, 3H), 4.76 (t, 1H), 6.74 (s, 1H), 7.30, (m, 2H), 7.73, (m, 7H), 8.47 (dd, 2H); $^{13}$C NMR (CD$_3$OD) ppm: 8.9, 20.0, 33.7, 38.0, 51.0, 88.8, 109.2, 113.3, 118.6, 125.5, 126.3, 126.7, 127.7, 129.0, 129.4, 134.1, 141.6, 145.4, 180.7, 189.8, 194.0; LRMS (FAB+, glycerol) M+=363 m/z (C$_{21}$H$_{19}$N$_2$O$_2$S).

(4-[3-methyl-2,3-dihydro-(benzo-1,3-thiazole)-2-methylidene]-1-quinolinium)-3-propionic N-hydroxysuccinimide ester (3). Compound 2 (100 mg) and 125 mg 1,3-dicyclohexylcarbodiimide (DCC, Fluka) were added to a dry mixture of dichloromethane, tetrahydrofuran, and N, N dimethyl formamide and allowed to stir one hour at room temperature under argon. After one hour, 65 mg of N-hydroxy-succinimide was added and stirring continued overnight. The dark red solution was filtered leaving the desired NHS ester in solution. Solvents were removed under high vacuum conditions to yield a glossy solid. This solid was dissolved in dichloromethane and 2-propanol and stored in a refrigerator. Two crops of precipitated solid material were recovered for a total yield of 50 mg (~40%). Both fractions were analyzed by Low Resolution Mass Spectrometry (LRMS), Fast Atom Bombardment (FAB$^+$) in glycerol. Both fractions showed M$^+$ of 460, though the first fraction was more pure. The second fraction contained a higher molecular weight impurity suggested by a peak at 569 m/z. High resolution FAB+MS confirmed the identity of the molecular ion for the first fraction: 460.13296 m/z; calculated for C$_{25}$H$_{22}$N$_3$O$_4$S: 460.13276.

Preparation of TO—Oligonucleotide Conjugates

TO-aminohexyl-5'-GTTCATCATCAGTAAC-3' (SEQ ID NO: 1) (4). The oligonucleotide was prepared using an ABI Aminolink 2™ phosphoramidite reagent at the 5' end of the sequence. This oligonucleotide corresponds to nucleotides 1820–1835 of pBR322 as published in Watson, N., *Gene* 70, 398 (1988) and NCBI—GenBank Flat File Release 74.0, a typical small DNA plasmid, and is representative of typical target sequences. The crude product was separated from the column by treatment with ammonium hydroxide for 8 hours at 55° C. After passing the resulting mixture through an 0.45 micron filter and evaporation of solvent, a crude oligonucleotide was obtained by ethanol precipitation. Approximately 0.5 umol of the oligonucleotide was dissolved in 100 uL sodium carbonate buffer at pH 9.0 in an Eppendorf tube. A 0.5 mg aliquot of TO-NHS (Compound 3) was dissolved in 30 uL DMSO, added to the tube, and the mixture was left at room temperature in the dark for 2 hours. The mixture was passed through a NAP-5 Sephadex column (Pharmacia LKB Biotechnology) and eluted with 10 mM TAE. The first 1.0 mL fraction was concentrated and purified by polyacrylamide gel electrophoresis.

TO-aminopropyl-5'-GGAATTCAGTTATCCACCAT-ACGGATAG-3' (SEQ ID NO: 2) (5). The oligonucleotide was linked to thiazole orange with a 3-carbon linker arm obtained as a protected phosphoramidite reagent from Glen Research. Positions 9–28 of this oligonucleotide correspond to a *Mycobacterium tuberculosis* IS6110 target sequence represented by nucleotides 993–1012 of the sequence published in Thierry, D., *Nuc. Acids Res.* 18, 188 (1990). Subsequent deprotection was accomplished by reaction of the completed oligo from its column material by concentrated ammonium hydroxide at 55° C. for six hours. Deprotection cleaves the oligonucleotide from the solid support and removes the trifluoroacetyl protecting group from the aminoalkyl linker's nitrogen. Following speed vacuum concentration and ethanol precipitation, the reactive primary amine on the oligonucleotide was ready for reaction with the TO-NHS. A solution of this reactive dye 5.9 mg/150 µl DMSO (d6) (85.5 mM) was prepared. A 50 µl aliquot of the oligonucleotide (0.25 µM) in H$_2$O was diluted with 50 µl of 250 mM sodium carbonate buffer at pH 9.0. To this 0.125 µM oligonucleotide solution was added 10 µl of the dye solution. After vortexing the Eppendorf tube, it was covered in aluminum foil and allowed to sit at room temperature for 15 hours. The crude product was purified by the same procedure as the preceding Example.

Similar thiazole yellow (TY)-oligonucleotide conjugates can be prepared by following the same procedures set forth above, but using N-methyl-benzoxazole-thiomethyl tosylate instead of N-methyl-benzothiazole-thiomethyl tosylate in the second step to produce compound 2. Compound 2 is then (4-[3-methyl-2,3-dihydro-(benzo-1,3-oxazole)-2-methylidene]-1-quinolinium)-3-propionic acid and compound 3 is (4-[3-methyl-2,3-dihydro-(benzo-1,3-oxazole)-2-methylidene]-1-quinolinium)-3-propionic acid N-hydroxy-succinimide ester.

EXAMPLE 2

Use of Thiazole Orange-Oligonucleotide Conjugates in Fluorescence Polarization Assays These experiments were performed on an SLM-Aminco model 8100 research grade spectrofluorometer with excitation at 510 nm. The fluorescence emission intensity was recorded from 515 to 600 nm and the fluorescence polarization was determined at 530 nm. The buffer for all measurements was 4 mM tris acetate, 0.1 mM EDTA, 50 mM NaCl at a pH of 7.8, and all measurements were at ambient temperature. The concentration of compound 5 (Example 1) and its complementary sequence were both 10 nM, with a sample size of 3 mL. Each value given for the fluorescence polarization is the average of three separate determinations.

Under these conditions the unhybridized probe (compound 5) showed a steady state fluorescence polarization of 320.7 mP (milli-polarization units). The complementary sequence to compound 5 was added and the mixture was incubated in the dark for 30 min. At this time the fluorescence polarization was recorded again and had increased to 357.0 mP. The fluorescence intensity was also recorded for both the unhybridized and hybridized solutions (see FIG. 1). At 530 nm the change in fluorescence intensity was approximately a 4-fold increase. This experiment demonstrates that hybridization of a thiazole-orange oligonucleotide conjugate may be easily detected by changes in fluorescence polarization, fluorescence intensity, or both.

EXAMPLE 3

Use of Thiazole Orange-Oligonucleotide Conjugates in Fluorescence Anisotropy Assays Compound 5 from Example 1 (a 28-mer conjugated to thiazole orange) was tested using time resolved fluorescence techniques. Specifically, dynamic anisotropy was determined using frequency domain instrumentation. This instrumentation measures the local molecular environment near the fluorophore (thiazole orange) determining different rotational correlation times resulting from larger/smaller molecules. The dynamic anisotropy decays are measured and then interpreted based on experimental fitting curves (in this case Global Analysis) applied to these observed decays. The following Table 1 shows the results of this dynamic anisotropy testing.

TABLE I

| TO-28 mer<br>Single Strand | T TO-28 mer/Complement<br>Double Strand |
|---|---|
| ∅ 3.4 ns (100%) | ∅₁ 0.5 ns (35%)<br>∅₂ 14.8 ns (65%) |

The results of this experiment show that progressively as one goes from (1) single-stranded cyanine dye-oligonucleotide conjugate to (2) double-stranded product from the hybridization of conjugate to nucleic acid sequence target, significant changes of the rotational correlation times occur that indicate the formation of larger, more structured molecules.

The invention disclosed herein is not limited in scope to the embodiments disclosed herein. Appropriate modifications, adaptations and expedients for applying the teachings herein in individual cases can be employed and understood by those skilled in the art, within the scope of the invention as claimed herebelow.

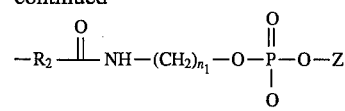

wherein X is O, S, Se, N-alkyl having from 1–6 carbons or $C(CH_3)_n$;

$R_1$ is alkyl having from 1–6 carbons;

$R_2$ is alkyl having from 1–6 carbons;

$R_3$ is fused benzene, alkyl having from 1–6 carbons, methoxy or is absent, $R_4$ is alkyl having from 1–6 carbons, methoxy or is absent;

Z is an oligonucleotide having from 8 to 50 bases;

---

---

What is claimed is:

1. A compound of the formula

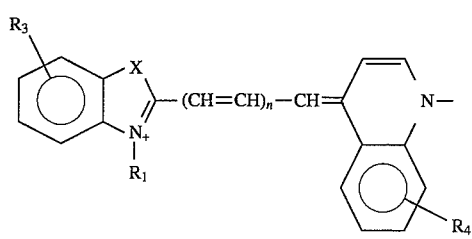

n is zero or an integer from 1–6; and $n_1$ is an integer from 2 to 10.

2. The compound of claim 1 wherein X is S.
3. The compound of claim 2 wherein $n_1$ is 3.
4. The compound of claim 2 wherein $n_1$ is 6.
5. The compound of claim 1 wherein X is O.
6. The compound of claim 5 wherein $n_1$ is 3.
7. The compound of claim 5 wherein $n_1$ is 6.
8. The compound of claim 1 wherein X is Se.
9. The compound of claim 8 wherein $n_1$ is 3.
10. The compound of claim 8 wherein $n_1$ is 6.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GTTCATCATC AGTAAC         16

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGAATTCAGT TATCCACCAT ACGGATAG         28